United States Patent [19]

Lantzsch et al.

[11] 4,423,225

[45] Dec. 27, 1983

[54] PROCESS FOR THE PREPARATION OF PYRAZOLE

[75] Inventors: Reinhard Lantzsch, Leverkusen; Klaus Ditgens, Wuppertal; Ulrich Heinemann, Wuppertal; Rudolf Thomas, Wuppertal; Erhard Weber, Wuppertal, all of Fed. Rep. of Germany

[73] Assignee: Bayer Aktiengesellschaft, Leverkusen, Fed. Rep. of Germany

[21] Appl. No.: 300,320

[22] Filed: Sep. 8, 1981

[30] Foreign Application Priority Data

Sep. 19, 1980 [DE] Fed. Rep. of Germany ....... 3035394

[51] Int. Cl.³ .......................................... C07D 231/12
[52] U.S. Cl. .................................................. 548/373
[58] Field of Search ........................................ 548/373

[56] References Cited

U.S. PATENT DOCUMENTS 2,515,160  7/1950  Copenhaver ........................ 548/373

FOREIGN PATENT DOCUMENTS 1234223  2/1967  Fed. Rep. of Germany .
2648008  5/1978  Fed. Rep. of Germany .
2704281  8/1978  Fed. Rep. of Germany .

OTHER PUBLICATIONS

Luttringhaus et al., Berichte 1959, vol. 92, pp. 1756–1765.
Ege, Tetrahedron Letters 1963, vol. 25, pp. 1665–1666.

Primary Examiner—Norma S. Milestone
Attorney, Agent, or Firm—Felfe & Lynch

[57] ABSTRACT

Process for the preparation of pyrazole by heating a pyrazoline derivative of the general formula

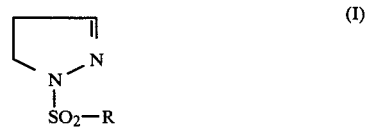

(I)

in which R represents an optionally substituted phenyl radical, or an alkyl or halogenoalkyl radical, without the addition of an acid or base, at a temperature between 100° and 200° C. under a pressure between 1 mbar and 10 bars, optionally in the presence of a diluent.

18 Claims, No Drawings

PROCESS FOR THE PREPARATION OF PYRAZOLE

This invention relates to a process for the preparation of pyrazole. This compound can be used as a starting material for the synthesis of herbicidally active acetanilides.

It has already been disclosed that pyrazole is obtained by splitting N-benzenesulphonyl-pyrazoline with an acid agent, such as, for example, hydrobromic acid (see Chem. Ber. 92, 1756 et seq. (1959)).

The preparation of substituted pyrazoles by splitting corresponding N-arylsulphonyl-pyrazolines in a basic medium, such as potassium hydroxide in glycol, a sodium alcoholate in alcohol or sodium hydroxide in water, is likewise known (see Tetrahedron Letters 25, 1665 (1963) and Zeitschrife für Chemie 5, 456 (1956)).

Both processes have the disadvantage that the unsubstituted pyrazole is obtained only in unsatisfactory yields. The yields are thus only less than 50%, even after careful working up.

The present invention now provides a process for the preparation of pyrazole from a pyrazoline derivative, characterised in that a pyrazoline derivative of the general formula

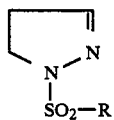

in which R represents an optionally substituted phenyl radical, or an alkyl or halogenoalkyl radical, is heated, without the addition of an acid or base, at a temperature between 100° and 200° C. and under a pressure between 1 mbar and 10 bars, optionally in the presence of a diluent.

It is to be described as exceptionally surprising that pyrazole is accessible by splitting pyrazoline derivatives of the formula (I) by means of heat, since, on the basis of the known state of the art, it was to be assumed that the reaction in question proceeds only when an acid or base is added to the rection mixture.

The process according to the invention is distinguished by a number of advantages.

Thus, it provides a possibility of preparing pyrazole in a simple manner in high yields, even on an industrial scale. Furthermore, apart from the diluent which is optionally to be used, it is not at all necessary to add any chemicals which could pollute the environment. Finally, after problem-free working up of the reaction mixture, the pyrazole is obtained in such a pure form that no additional purification is necessary. The process according to the invention thus represents a valuable enrichment of the art.

If, for example, N-benzenesulphonylpyrazoline is used as the starting substance, the process according to the invention can be represented by the following equation:

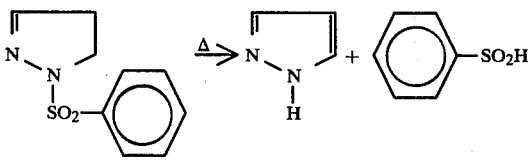

Preferred pyrazoline derivatives of formula (I) to be used as starting substances for the process according to the invention are those in which R represents a phenyl radical which is optionally substituted by alkyl with 1 to 4 carbon atoms or halogen, an alkyl radical with 1 to 4 carbon atoms or a perfluoroalkyl radical with 1 to 4 carbon atoms.

Those pyrazoline derivatives of the formula (I) in which R represents a phenyl radical which is optionally substituted by methyl or chlorine, or a methyl or trifluoromethyl radical are particularly preferred.

The pyrazoline derivatives of the formula (I) are known, and are obtained in a known manner by reacting pyrazoline with the corresponding sulphonic acid chlorides (in this context, see also the abovementioned literature references and the following Preparative Examples). If appropriate, the pyrazoline derivatives of the formula (I) can also be pyrolysed directly in a further reaction, without being isolated, to give the pyrazole.

If appropriate, the process according to the invention is carried out in the presence of a diluent. Preferred possible solvents for the reaction are aromatic hydrocarbons, such as toluene, xylene, chlorobenzene or dichlorobenzene, but in particular also mixtures of water and one of the abovementioned aromatic hydrocarbons.

The process according to the invention is carried out under the specified reduced or increased pressure. In general, it is carried out between 1 mbar and 500 mbars if no diluent is used, and between normal pressure and 10 bars if a diluent is used.

The reaction temperatures can be varied within the substantial range of between 100° and 200° C. in carrying out the process according to the invention, preferably at a temperature between 140° and 180° C.

If the process according to the invention is carried out without a diluent, a procedure is generally followed in which the starting material of the formula (I) is heated under reduced pressure in a distillation apparatus. The pyrazole formed thereby distils off and is collected in a highly pure state.

If the process according to the invention is carried out in the pressure of a diluent, a procedure is generally followed in which the starting material of the formula (I) is dissolved or suspended in the particular diluent and the reaction mixture is heated in a closed apparatus under the resulting autogenous pressure. Working up is effected by customary methods. In general, a procedure is followed in which the reaction mixture is treated with an aqueous alkali metal base and is then extracted with an organic solvent which has a low miscibility with water, and the solvent is then distilled off from the organic phase. The pyrazole obtained is already very pure, and usually does not have to be purified further by distillation. It is also possible for the reaction mixture to be concentrated after the treatment with an aqueous alkali metal base and for the residue which remains to be distilled.

The pyrazole which can be prepared by the process according to the invention is a generally interesting synthesis unit in organic chemistry. In particular, pyrazole can be used as a starting substance for the synthesis of herbicidally active acetanilides (see DE-OS (German Published Specification) No. 2,648,008 and DE-OS (German Published Specification) No. 2,704,281).

Thus, for example, 2,6-diethyl-N-(pyrazol-1-yl-methyl)-chloroacetanilide can be prepared by reacting 2,6-diethyl-N-chloromethyl-chloroacetanilide with pyrazole in the presence of a diluent and in the presence of an acid-binding agent. This synthesis can be represented by formulae as follows:

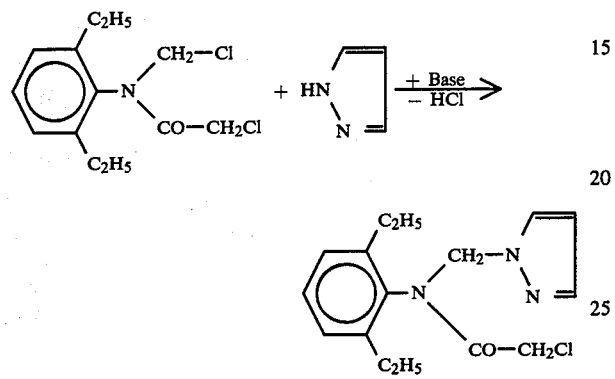

The process according to the invention is illustrated by the following examples.

PREPARATIVE EXAMPLES

Example 1

63 g (0.3 mole) of benzenesulphonylpyrazoline were heated to 150° C./10 mm Hg in a distillation apparatus. A slightly yellowish liquid distilled over and crystallised after a short time. 14.7 g (72% of theory) of pyrazole of melting point 69° C. were obtained.

Example 2

4.2 g (62% of theory) of pyrazole of melting point 70° C. were obtained from 14.8 g (0.1 mole) of methanesulphonylpyrazoline, in a manner corresponding to that in Example 1.

Preparation of the starting material 114.5 g of methanesulphonic acid chloride were added dropwise to 70 g of pyrazoline and 101 g of triethylamine in 300 ml of methylene chloride at room temperature. The mixture was subsequently stirred at room temperature for 3 hours and was filtered. The filtrate was washed with water, dried over sodium sulphate and concentrated. 114 g (77% of theory) of methanesulphonylpyrazoline of melting point 62° C. were obtained.

Example 3

105 g (0.5 mole) of benzenesulphonylpyrazoline were suspended in 950 ml of water and the suspension was heated to 150° C., a pressure of 5 bars being reached. Quantitative analysis by gas chromatography using an internal standard gave 32 g (94.1% of theory) of pyrazole. The reaction solution was then allowed to cool and was rendered weakly alkaline by adding sodium hydroxide solution and extracted with methylene chloride in a perforator (apparatus for continuous extraction). 30.9 g (91% of theory) of pyrazole of melting point 70° C. were obtained.

Example 4

65.12 g (0.44 mole) of methanesulphonylpyrazoline were suspended in 590 ml of water and the suspension was heated to 145° C. for one hour, a pressure of 10 bars being reached. After cooling, the reaction mixture was rendered weakly alkaline with sodium hydroxide solution. Quantitative analysis by gas chromatography using an internal standard showed that 27.4 g (91.6% of theory) of pyrazole had been formed. The pyrazole was isolated by extraction with methylene chloride.

Example 5

21 g (0.1 mole) of benzenesulphonylpyrazoline were suspended in 190 g of xylene (isomer mixture) and the suspension was heated to the boiling point for one hour. Water was added and the mixture was rendered weakly alkaline, whilst stirring. The organic phase was separated off and the aqueous phase was extracted five times more by shaking with methylene chloride. The combined organic phases were dried and distilled. 5.7 g (83.8% of theory) of pyrazole were obtained.

COMPARISON EXAMPLES, SHOWING THE SYNTHESIS OF PYRAZOLE BY KNOWN METHODS

Example A 21 g (0.1 mole) of benzenesulphonylpyrazoline were dissolved in a solution of 5.4 g (0.1 mole) of sodium methylate in 200 ml of methanol. The solution was heated to the boiling point for one hour. After cooling, a clear solution was obtained. Quantitative analysis by gas chromatography using an internal standard showed that 1.78 g (26.2% of theory) of pyrazole had been formed. The mixture was diluted with water and extracted with methylene chloride in a perforator. After distilling off the solvent, an oil remained, from which 1.1 g of pyrazole could be isolated by distillation (bulb tube).

Example B 21 g (0.1 mole) of benzenesulphonylpyrazoline were suspended in 40 g of 10% strength hot sodium hydroxide solution, whereupon a clear solution was formed. The reaction solution was kept at 75° C. for a further short period and was then allowed to cool. Quantitative analysis by gas chromatography, using an internal standard showed that 3.16 g (46% of theory) of pyrazole had been formed. The water was distilled off from the clear solution in vacuo at a bath temperature of 45° C.; the residue was digested several times with ether. The combined ether extracts were dried over sodium sulphate and concentrated. 2.9 g of pyrazole of melting point 65°–66° C. were obtained.

Example C 10.5 g of benzenesulphonyl-pyrazoline were boiled under reflux with 60 ccs of 48 percent strength hydrobromic acid for 2 hours. Diphenyl disulphide separated out and, after cooling, solidified. The solid was filtered off; melting point, from alcohol: 61° C. (literature; 61° C.). Yield: 1.2 g (22% of theory, relative to the benzenesulphonyl derivative). The diphenyl disulphide was reduced to the thiophenol with zinc in hydrochloric acid.

The filtrate was freed from the hydrobromic acid in vacuo and the white residue was triturated with an excess of 50 percent strength sodium hydroxide solution. The triturated mixture was then allowed to drip into a flask containing about 50 ccs of ether, and vigorous stirring was carried out. Both components had to be mixed thoroughly. The mixture was then allowed to settle and the ether was decanted; the same operation was repeated again with fresh ether. The two extracts were combined, and dried over sodium sulphate: they gave crude pyrazole, melting point: 65° C., yield: 1.6 g (47% of theory, relative to the benzenesulphonyl derivative of the pyrazoline). From ligroin, white needles of melting point 69° C.

EXAMPLE OF THE USE OF PYRAZOLE FOR THE SYNTHESIS OF A HERBICIDALLY ACTIVE ACETANILIDE

Example I

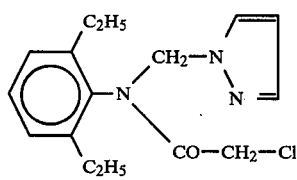

A mixture of 68 g (1 mole) of pyrazole and 106 g (1.05 moles) of triethylamine in 150 ml of anhydrous ethyl acetate was added to 274.2 g (1 mole) of 2,6-diethyl-N-chloromethyl-chloroacetanilide in 250 ml of anhydrous ethyl acetate, whilst stirring, during which the temperature rose to 30° C. The mixture was subsequently stirred at room temperature for 1 hour. There were two possibilities for working up:

(a) The reaction mixture was filtered and the filtrate was washed with water until neutral, dried over sodium sulphate and evaporated in vacuo. After fractional crystallisation with ligroin, 171.2 g (56% of theory) of 2,6-diethyl-N-(pyrazol-1-yl-methyl)-chloroacetanilide of melting point 67° C. were obtained in the form of colourless crystals.

(b) The reaction mixture was cooled to 0° C. and filtered and the residue on the filter was rinsed with 10 ml of cold ethyl acetate. 50 g (1.4 moles) of dry hydrogen chloride were passed into the filtrate at 0° to −10° C. The hydrochloride salts which had precipitated were then filtered off and rinsed with 50 ml of cold ethyl acetate and the solid residue was partitioned between 0.5 liter of ethyl acetate and 0.5 liter of aqueous sodium hydroxide solution with a pH value of 12. The organic phase was separated off, washed twice with 0.5 liter of sodium chloride solution each time, dried over sodium sulphate and evaporated in vacuo. 60 ml of benzine were added to the colourless, oily residue, whereupon it crystallised. 220.2 g (72% of theory) of 2,6-diethyl-N-(pyrazol-1-yl-methyl)-chloroacetanilide of melting point 67° C. were obtained in the form of colourless crystals.

It will be understood that the specification and examples are illustrative but not limitative of the present invention and that other embodiments within the spirit and scope of the invention will suggest themselves to those skilled in the art.

What is claimed in:

1. Process for the preparation of pyrazole which comprises heating a pyrazoline derivative of the formula

wherein R is optionally substituted phenyl or alkyl or haloalkyl without the addition of an acid or base, at a temperature between 100° and 200° C. and under a pressure between 1 mbar and 10 bars.

2. Process as claimed in claim 1 wherein, in formula (I) R, is phenyl.

3. Process as claimed in claim 1 wherein, in formula (I), R is phenyl substituted with alkyl of 1 to 4 carbon atoms or halogen.

4. Process as claimed in claim 1 wherein, in formula (I), R is alkyl of 1 to 4 carbon atoms.

5. Process as claimed in claim 1 wherein, in formula I R is perfluoroalkyl of 1 to 4 carbon atoms.

6. Process as claimed in claim 1 wherein, in formula I R is phenyl substituted by methyl or chlorine.

7. Process as claimed in claim 1 wherein, in formula I R is phenyl substituted by methyl or trifluoromethyl.

8. Process as claimed in claim 1 wherein, the reaction is carried out at a temperature between 140° C. and 180° C.

9. Process as claimed in claim 1 wherein, the reaction is carried out in the absence of a diluent.

10. Process as claimed in claim 1 wherein, the reaction is carried in the presence of a diluent.

11. Process as claimed in claim 10 wherein, the diluent is water.

12. Process as claimed in claim 10 wherein, the diluent is a solvent selected from toluene, xylene, chlorobenzene and dichlorobenzene.

13. Process as claimed in claim 10 wherein the diluent is a solvent selected from toluene, xylene, chlorobenzene and dichlorobenzene in admixture with water.

14. Process as claimed in claim 1 wherein benzenesulphonylpyrazoline is heated to 150° C., to provide pyrazole.

15. Process as claimed in claim 1 wherein methanesulphonyl pyrazoline is heated to 150° C., to provide pyrazole.

16. Process as claimed in claim 1 wherein benzenesulphonylpyrazoline is suspended in water, the suspension is heated to 150° C. at a maximum pressure of 5 bars, to provide pyrazole.

17. Process as claimed in claim 1 wherein methanesulphonylpyrazoline is suspended in water and heated to 145° C. at a maximum pressure of 10 bars, to provide pyrazole.

18. Process as claimed in claim 1 wherein benezenesulphonylpyrazoline is suspended in xylene and heated, to provide pyrazole.

* * * * *